United States Patent [19]

Son et al.

[11] Patent Number: 4,687,850

[45] Date of Patent: Aug. 18, 1987

[54] PURIFICATION OF 1-(2-AMINO-2-ALKYLPROPYL)-3,3,5,5-TETRAALKYLPIPERAZINONES

[75] Inventors: Pyong-Nae Son, Akron; Charles P. Jacobs, Elyria, both of Ohio

[73] Assignee: The B.F. Goodrich Company, Akron, Ohio

[21] Appl. No.: 677,667

[22] Filed: Dec. 3, 1984

[51] Int. Cl.$^4$ ............................................. C07D 241/08
[52] U.S. Cl. ...................................... 544/384; 544/231
[58] Field of Search .............................. 544/231, 384

[56] References Cited

U.S. PATENT DOCUMENTS 4,167,512  9/1979  Lai ........................................ 544/384

*Primary Examiner*—Glennon H. Hollrah
*Assistant Examiner*—James H. Turnipseed
*Attorney, Agent, or Firm*—Carl W. Battle; George A. Kap; Alan A. Csontos

[57] ABSTRACT

Novel piperazinones having the formula

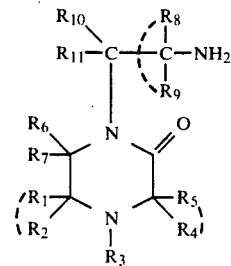

are useful UV stabilizers and are purified by fractional distillation in the presence of an inorganic base.

7 Claims, No Drawings

PURIFICATION OF 1-(2-AMINO-2-ALKYLPROPYL)-3,3,5,5-TETRAALKYLPIPERAZINONES

BACKGROUND OF THE INVENTION

The increasing use of polymers in place of the more traditional types of structural materials (e.g. wood, metals, etc.) has necessitated the compounding of such polymers with a variety of stabilizers in order to enhance the ability of such polymers to withstand prolonged exposure to a variety of degradative forces. Degradation of such environmentally sensitive polymers can be caused by exposure to light, heat and/or air. Such degradation is usually manifest by either a partial or total loss of structural integrity, changes in light transmission properties, changes in color, loss or reduction in flexibility and/or resiliency, or any combination of the above phenomenon. As will be appreciated, the stabilizers which are used in conjunction with the above polymeric materials, in addition to providing protection against such degradative changes, must also be compatible with the aesthetic properties of the polymeric article and be effective at low concentrations. The economics of the marketplace dictate that these stabilizers be relatively inexpensive and capable of preparation from readily available starting materials by simple and straightforward synthesis techniques.

The diazacycloalkanones have been found to be highly effective in the stabilization of polymeric materials against the photodegradative forces of ultraviolet light. The efficacy of such materials in the UV stabilization of polymers is described in U.S. Pat. No. 4,190,571, the disclosure of which is herein incorporated by reference. Specifically, the '571 patent teaches the preparation of 2-keto-1,4-diazacycloalkanes, such as 1-propyl-3,3,5,5-tetramethyl-2-piperazinone, by reaction of an appropriate 1,2-diamine with acetone cyanohydrin in the presence of sodium hydroxide and benzyltriethylammonium chloride. The crude reaction product is typically distilled to yield the purified substituted-piperazinone product. U.S. Pat. No. 4,297,497, which is incorporated by reference, teaches the synthesis of related 2-keto-1,4-diazocycloalkanes by reacting a 1,2-diamine, a monoketone and haloform in the presence of alkali and phase transfer catalyst, and subsequent distillation to obtain the purified product.

The present invention relates to the purification of a novel class of 1-(2-amino-2-alkylpropyl)-3,3,5,5-tetraalkylpiperazinones. The novel compounds are prepared by reacting an appropriate 1,2-propanediamine with a ketone and a haloform in the presence of alkali as described in U.S. patent application Ser. No. 664,901, filed Oct. 26, 1984, now U.S. Pat. No. 4,547,538. This reaction yields a crude reaction product having a 75–85% purity. For practical applications, the crude reaction product is separated from the aqueous layer and purified by fractional distillation, which results in a maximum purity of about 90% and the formation of undesirable side-products. Through this invention, it was unexpectedly discovered that if the fractional distillation was carried out in the presence of an inorganic base, a product having a purity as high as 96% was obtained while suppressing the formation of undesirable side-products.

It is the object of the present invention to provide an improved process for purification of the substituted amino-alkyl-piperazinones comprising fractional distillation in the presence of an inorganic base. These piperazinones are useful as UV stabilizers and as intermediates for preparing a variety of high molecular weight polymer stabilizers.

SUMMARY OF THE INVENTION

This invention relates to a process for purification of novel substituted amino-alkyl-piperazinones which have the formula

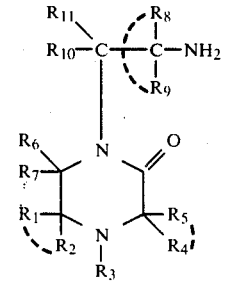

wherein $R_1$, $R_2$, $R_4$ and $R_5$ independently represent alkyl, haloalkyl, cyanoalkyl, cycloalkyl, hydroxycycloalkyl, aminoalkyl and alkenyl, most preferably methyl; $R_3$ represents hydrogen, alkyl, hydroxyalkyl, haloalkyl, cyanoalkyl, aminoalkyl, alkenyl, aralkyl, and carboalkoxy, most preferably hydrogen; $R_6$, $R_7$, $R_{10}$ and $R_{11}$ independently represent hydrogen, alkyl, haloalkyl, cyanoalkyl, aminoalkyl, cycloalkyl, alkenyl and aralkyl, most preferably hydrogen; $R_8$ and $R_9$ independently represent hydrogen or alkyl, most preferably methyl; and further that $R_1$ and $R_2$, $R_4$ and $R_5$, and $R_8$ and $R_9$ independently can form a 4 to 12 member ring. These novel compounds are useful as UV stabilizers and as intermediates in preparing a variety of high molecular weight stabilizers. They are purified by the process of the present invention up to a purity of about 96% by fractional distillation in the presence of an inorganic base.

DETAILED DESCRIPTION

This invention relates to the purification of novel 1-(2-amino-2-alkylpropyl)-3,3,5,5-tetraalkylpiperazinones and derivatives thereof which find utility as UV stabilizers and as intermediates in the preparation of relatively high molecular weight piperazinone stabilizers. The novel piperazinones which can be purified by the process of the present invention may be represented by the general formula

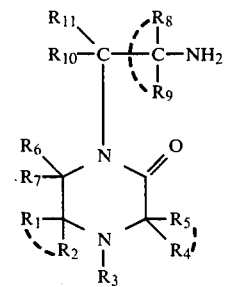

wherein $R_1$, $R_2$, $R_4$ and $R_5$ independently represent alkyl, haloalkyl, cyanoalkyl, cycloalkyl, hydroxycycloalkyl, aminoalkyl and alkenyl; $R_3$ represents hydrogen, alkyl, hydroxyalkyl, haloalkyl, cyanoalkyl, aminoalkyl, alkenyl, aralkyl and carboalkoxy; $R_6$, $R_7$, $R_{10}$ and $R_{11}$ independently represent hydrogen, alkyl, haloalkyl, cyanoalkyl, aminoalkyl, cycloalkyl, alkenyl and aralkyl; $R_8$ and $R_9$ independently represent hydrogen or alkyl; and further that $R_1$ and $R_2$, $R_4$ and $R_5$, and $R_8$ and $R_9$ independently can form a 4 to 12 member ring.

Preferably $R_1$, $R_2$, $R_4$ and $R_5$ independently represent alkyl or haloalkyl having from 1 to about 12 carbon atoms, cyanoalkyl or aminoalkyl having from 2 to about 12 carbon atoms, cycloalkyl or hydroxy-cycloalkyl having from 5 to about 14 carbon atoms, and alkenyl having from 7 to about 14 carbon atoms. Preferably $R_3$ represents hydrogen, alkyl having from 1 to about 24 carbon atoms; hydroxyalkyl, haloalkyl, or aminoalkyl having from 1 to about 12 carbon atoms; cyanoalkyl having from 2 to about 12 carbon atoms, and alkenyl or aralkyl having from 7 to about 14 carbon atoms. Preferably $R_6$, $R_7$, $R_{10}$ and $R_{11}$ independently represent hydrogen, alkyl or haloalkyl having from 1 to about 12 carbon atoms, cyanoalkyl or aminoalkyl having from 2 to about 12 carbon atoms, cycloalkyl having from 5 to about 14 carbon atoms, and alkenyl or aralkyl having from 7 to about 14 carbon atoms. Preferably $R_8$ and $R_9$ independently represent hydrogen or alkyl having from 1 to about 12 carbon atoms. Most preferably, $R_1$, $R_2$, $R_4$, $R_5$, $R_8$ and $R_9$ independently are methyl, and $R_3$ is hydrogen.

Typically the aminoalkylpiperazinones are prepared in crude form having a purity generally from about 75 to 85%. Following the separation of any aqueous layer, the crude reaction product is usually purified further by fractional distillation of the organic components. However, fractional distillation results in a desired product having a maximum purity of only about 90%. This deficiency in purification results from the formation of undesirable side-products during the distillation, such as, for example, those having the formula

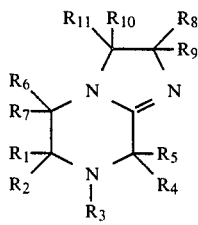

wherein $R_1$–$R_{11}$ are as defined earlier.

To minimize the formation of the above side-products, it is critical in the practice of this invention to carry out the fractional distillation in the presence of an inorganic base. The base inhibits the formation of undesirable side-products during the fractional distillation step. The use of a base during distillation also results in a final product having up to about 96% purity and an improved yield.

The inorganic bases which are suitable for use in this invention include the hydroxides, oxides, carbonates, and bicarbonates of the Group IA and Group IIA metals of the periodic table. The base may include, for example, compounds having the formulas $M(OH)_n \cdot nH_2O$, $M_nCO_3$, $M_nHCO_3$, $M_nO$ and the like, wherein M represents a Group IA or Group IIA metal and n represents an integer from about 1 to about 10. Preferably the base includes a metal selected from sodium, potassium, barium or calcium. The amount of inorganic metallic base used in the fractional distillation is not critical, but preferably the amount ranges from about 0.004 moles to about 0.01 moles of base per mole of aminoalkyl-piperazinone. The base is preferably added to the crude organic reaction product in solid form and fractional distillation is carried out by any methods known in the art.

The following examples are presented to illustrate this invention, and are intended in an illustrative and not limitative sense.

EXAMPLE I–V

In Examples I–V, crude 1-(2-amino-2-methylpropyl)-3,3,5,5-tetramethylpiperazinone, prepared as described in U.S. patent application Ser. No. 664,901, filed Oct. 26, 1984, now U.S. Pat. No. 4,547,538, and having a purity of 76–78%, was distilled using a 4 inch length by 1 inch diameter distillation column packed with stainless steel protruded packing. In all Examples 50 grams of crude 1-(2-amino-2-methylpropyl)-3,3,5,5-tetramethylpiperazinone was used which distilled at 110°–112° C. The distilled product was analyzed for purity by gas chromatography, and the results are given in Table I below:

TABLE I

| Example | Purity of Crude Product | Metallic Base | Maximum Purity of Distilled Product | Yield |
|---|---|---|---|---|
| I | 78% | None | 90% | 17.0 grams |
| II | 78% | $Ba(OH)_2 \cdot H_2O$ 1.5 g. (0.008 mole) | 95% | 28.2 grams |
| III | 76% | NaOH 0.32 g. (0.008 mole) | 96% | 31.2 grams |
| IV | 76% | $Ca(OH)_2$ 0.59 g. (0.008 mole) | 95% | 29.4 grams |
| V | 76% | $Ba(OH)_2 \cdot 8H_2O$ 1.25 g. (0.004 mole) | 95% | 25.5 grams |

The above Examples demonstrate the effectiveness of the inorganic bases in obtaining a high purity product. The use of the base in Examples II–V results in a 95–96% purity in comparison to a maximum purity of about 90% in Example I where no base is used. Additionally the base leads to an improvement in recovery of the distilled product in the magnitude of about 65 to about 85%.

We claim:

1. In a process for purification of substituted amino-alkyl-piperazinones by fractional distillation, the improvement which comprises carrying out said distillation in the presence of an inorganic base.

2. A process of claim 1 wherein said substituted amino-alkyl-piperazinones have the formula

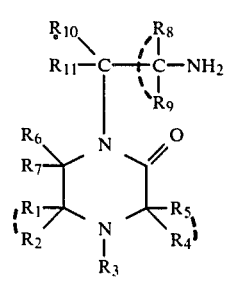

wherein $R_1$, $R_2$, $R_4$ and $R_5$ independently represent alkyl, haloalkyl, cyanoalkyl, cycloalkyl, hydroxycycloalkyl, aminoalkyl and alkenyl; $R_3$ represents hydrogen, alkyl, hydroxyalkyl, haloalkyl, cyanoalkyl, aminoalkyl, alkenyl, aralkyl and carboalkoxy; $R_6$, $R_7$, $R_{10}$ and $R_{11}$ independently represent hydrogen, alkyl, haloalkyl, cyanoalkyl, aminoalkyl, cycloalkyl, alkenyl and aralkyl; $R_8$ and $R_9$ independently represent hydrogen or alkyl; and further that $R_1$ and $R_2$, $R_4$ and $R_5$, and $R_8$ and $R_9$ independently can form a 4 to 12 member ring.

3. A process of claim 2 wherein the substituted amino-alkyl-piperazinone has the formula

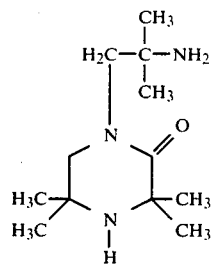

4. A process of claim 1 wherein the inorganic base is a metal hydroxide, oxide, carbonate, or bicarbonate.

5. A process of claim 4 wherein the concentration of said base ranges from about 0.005 moles to about 0.01 moles per mole of the piperazinone compound.

6. A process of claim 4 wherein the metal is selected from the Group IA and Group IIA elements of the periodic table.

7. A process of claim 6 wherein the metal is selected from the group consisting of barium, sodium, calcium and potassium.

* * * * *